(12) United States Patent
Macina et al.

(10) Patent No.: US 6,228,596 B1
(45) Date of Patent: May 8, 2001

(54) METHOD OF DETECTING AND MONITORING ENDOMETRIAL AND UTERINE CANCERS

(75) Inventors: Roberto A. Macina, Santa Jose; John D. Burczak, Santa Clara, both of CA (US)

(73) Assignee: diaDexus, Inc., Santa Clara, CA (US)

( * ) Notice: Subject to any disclaimer, the term of this patent is extended or adjusted under 35 U.S.C. 154(b) by 0 days.

(21) Appl. No.: 09/623,293

(22) PCT Filed: Feb. 17, 1999

(86) PCT No.: PCT/US99/03323

§ 371 Date: Sep. 1, 2000

§ 102(e) Date: Sep. 1, 2000

(87) PCT Pub. No.: WO99/45147

PCT Pub. Date: Sep. 10, 1999

Related U.S. Application Data

(60) Provisional application No. 60/076,925, filed on Mar. 5, 1998.

(51) Int. Cl.$^7$ .......................... C12Q 1/68; G01N 33/574
(52) U.S. Cl. .................................. 435/6; 435/7.23
(58) Field of Search ........................... 435/6, 91.1, 7.23; 536/22.1, 23.1

(56) References Cited

FOREIGN PATENT DOCUMENTS

WO 97/34997    9/1997  (WO) .

*Primary Examiner*—Eggerton A. Campbell
(74) *Attorney, Agent, or Firm*—Licata & Tyrrell P.C.

(57) ABSTRACT

The present invention provides a new method for diagnosing cancers, particulary endometrial and uterine cancer.

6 Claims, No Drawings

METHOD OF DETECTING AND MONITORING ENDOMETRIAL AND UTERINE CANCERS

This application is a 371 of PCT/US99/03323 filed Feb. 17, 1999, which claims benefit of Provisional No. 60/076,925 filed Mar. 5, 1998.

FIELD OF THE INVENTION

This invention relates, in part, to a newly developed assay for diagnosing cancers, particularly endometrial and uterine cancer.

BACKGROUND OF THE INVENTION

Endometrial cancer occurs at a rate of approximately 44,500 new cases per year with approximately 10,000 deaths per year. If diagnosed and treated early, when the cancer is still confined to the endometrium, cure can be achieved in approximately 95% of the cases by hysterectomy. Pap smears can show endometrial cancers but are effective in only 50% of the cases. For the remainder, abnormal vaginal bleeding is typically the first clinical sign of endometrial cancer. There is a great need for sensitive methods for the detection of organ-confined endometrial cancer.

Sarcoma of the uterus, a very rare kind of cancer in women, is a disease in which cancer (malignant) cells start growing in the muscles or other supporting tissues of the uterus. Sarcoma of the uterus is different from cancer of the endometrium, a disease in which cancer cells start growing in the lining of the uterus. Women who have received therapy with high-dose x-rays (external beam radiation therapy) to their pelvis are at a higher risk to develop sarcoma of the uterus. These x-rays are sometimes given to women to stop bleeding from the uterus. Like most cancers, sarcoma of the uterus is best treated when it is found (diagnosed) early. Sarcoma of the uterus usually begins after menopause.

When a patient has signs of such cancer, the doctor will do certain tests to check for cancer, usually beginning with an internal (pelvic) exam. During the exam, the doctor will feel for any lumps or changes in the shapes of the pelvic organs. The doctor may then do a Pap test. Because sarcoma of the uterus begins inside, this cancer will not usually show up on the Pap test. The doctor may also do a dilation and curettage (D & C) by stretching the cervix and inserting a small, spoon-shaped instrument into the uterus to remove pieces of the lining of the uterus. This tissue is then checked under a microscope for cancer cells.

Prognosis (chance of recovery) and choice of treatment depend on the stage of the sarcoma (whether it is just in the uterus or has spread to other places), how fast tumor cells are growing, and the general state of the patient's health.

As noted, treatment decisions for an individual are linked to the stage of such cancer present in that individual. However, current endometrial and uterine cancer staging methods are limited and some such cancers initially staged as not metastatic are, in fact, metastatic. Discovery of metastasis is significant because patients with metastatic cancers have a poorer prognosis and require significantly different therapy than those with localized cancers.

Accordingly, not only is there a need for more sensitive methods of diagnosing these cancers, but there is also a great need for sensitive methods for staging of an endometrial or uterine cancer in a human to determine whether or not such cancer has metastasized and for monitoring the progress of such cancer in a human which has not metastasized for the onset of metastasis.

Steroid binding proteins, including uteroglobin and CC10, are a class of proteins which bind steroids along with methylsulfonyl metabolites of polychlorinated biphenyls. The exact function of members of this class of proteins is uncertain. Uteroglobin has been shown to inhibit PLA2 mediated responses.

Gene and gene products useful in the present invention display homology to uteroglobin and CC10, show elevated expression of mRNA in endometrial cancer samples and are expressed in mammary tissue. These gene and gene products are described in published patent application WO 97/34997 entitled Human Endometrial Specific Steroid Binding Factors I, II and III which is incorporated herein by reference. The genes and their encoded products are referred to herein as Human Endometrial Specific Steroid-Binding Factor I (hESF I) which corresponds to Human Endometrial Specific Steroid-Binding Factor I (hESF I) published in WO 97/34997. WO 97/34997 teaches that detection of mutated forms of hESF I, II, and III associated with a dysfunction will provide a diagnostic tool that can add to and define diagnosis of a disease or susceptibility of a disease which result from under-expression, over-expression or altered expression of hESF-I, II and II. For example, it is suggested that detection of a mutated gene may be indicative of a susceptibility to inherited asthma or endometrial cancer. WO 97/34997 also discloses a diagnostic assay for detection of over-expression or under-expression of hESF I, II and III protein for use in detection of the presence of neoplasia.

It has now been found that hESF I is useful as cancer marker for diagnosing endometrial and uterine cancer.

SUMMARY OF THE INVENTION

Toward these ends, and others, it is an object of the present invention to provide a method for detecting the expression of the cancer marker hESF I in a patient which comprises taking a sample derived from a patient and detecting in the sample a nucleic acid sequence encoding hESF I or a protein product encoded by a hESF I nucleic acid sequence.

Another object of the present invention is to provide a diagnostic method for detecting the presence of endometrial cancer and/or uterine cancer in a patient suspected of suffering from endometrial cancer and/or uterine cancer which comprises measuring levels of hESF I polypeptide in cells, tissues or bodily fluids obtained from a patient suspected of suffering from endometrial and/or uterine cancer; and comparing the measured levels of hESF I polypeptide with levels of hESF I in normal cells, tissues or bodily fluids, wherein an increase in hESF I polypeptide levels in the patient versus levels of hESF I polypeptide in normal cells, tissues or bodily fluids is indicative of endometrial cancer and/or uterine cancer.

Another object of the present invention is to provide a diagnostic method for detecting the presence of endometrial cancer and/or uterine cancer in a patient suspected of suffering from endometrial cancer and/or uterine cancer which comprises measuring transcription levels of hESF I in cells, tissues or bodily fluids of a patient suspected of suffering from endometrial and/or uterine cancer; and comparing the measured transcription levels of hESF I with hESF I transcription levels in normal cells, tissues or bodily fluids, wherein an increase in hESF I transcription levels in the patient versus normal hESF I transcription levels is associated with endometrial cancer and/or uterine cancer.

Another object of the present invention is to provide a method of monitoring endometrial and/or uterine cancer in a patient which has not metastasized for the onset of metastasis which comprises identifying a patient suffering from endometrial cancer and/or uterine cancer that is not known to have metastasized; measuring hESF I levels in a sample of bodily fluid from said patient; and comparing the measured hESF I levels in said patient with levels of hESF I in the same bodily fluid type from a normal control sample, wherein an increase in measured hESF I levels in the patient versus hESF levels in the normal control sample is associated with a cancer which has metastasized.

Yet another object of the present invention is to provide a method of monitoring the stage of endometrial cancer and/or uterine cancer in a patient suffering from endometrial cancer or uterine cancer which comprises identifying a patient suffering from endometrial cancer and/or uterine cancer; determining hESF I levels in a sample of bodily fluid from said patient to establish a baseline hESF I level for said patient; measuring hESF I levels in samples of the same bodily fluid from said patient at subsequent time periods; and comparing the measured hESF I levels with the baseline hESF I levels, wherein an increase in measured hESF I levels in the patient versus baseline hESF I levels in the patient is associated with a cancer which is progressing and a decrease in measured hESF I levels versus baseline hESF I levels is associated with a cancer which is regressing or in remission.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DESCRIPTION OF THE INVENTION

The present invention relates to diagnostic assays, both quantitative and qualitative for detecting levels of hESF I polypeptide or hESF I nucleic acids in cells, tissues and bodily fluids, including determination of normal and abnormal levels. By "hESF I polypeptide" is meant a protein or fragment thereof having an amino acid sequence identical to or substantially similar to that disclosed for hESF I in WO 97/34997. Polypeptides which are "substantially similar" to the hESF I protein disclosed in WO 97/34997 may contain conservative amino acid substitutions which do not alter the structure or activity of the hESF I protein. By "hESF I nucleic acids" is it meant to include both RNA and DNA encoding the hESF I protein as disclosed in WO 97/34997 or a polypeptide with the same structure and activity. Thus, a diagnostic assay in accordance with the present invention for detecting over-expression of an hESF I polypeptide compared to normal control bodily fluids or tissue samples via detection of elevated polypeptide or transcription levels may be used to detect the presence of cancers, including endometrial and uterine cancer.

Assay techniques that can be used to determine levels of a polypeptide or transcription levels of a gene, such as hESF I of the present invention, in a sample derived from a host are well-known to those of skill in the art. Such assay methods include, but are not limited to, radioimmunoassays, reverse transcriptase PCR (RT-PCR) assays, gridding, immunohistochemistry assays, in situ hybridization assays, competitive-binding assays, Western Blot analyses and ELISA assays. Among these, ELISAs are frequently preferred to detect a gene's expressed protein in biological fluids. An ELISA assay initially comprises preparing an antibody, if not readily available from a commercial source, specific to hESF I, preferably a monoclonal antibody. In addition, a reporter antibody generally is prepared which binds specifically to hESF I. The reporter antibody is attached to a detectable reagent such as a radioactive, fluorescent or enzymatic reagent, for example horseradish peroxidase enzyme or alkaline phosphatase.

To carry out the ELISA, antibody specific to hESF I is incubated on a solid support, e.g., a polystyrene dish, that binds the antibody. Any free protein binding sites on the dish are then covered by incubating with a non-specific protein such as bovine serum albumin. Next, the sample to be analyzed is incubated in the dish, during which time hESF I binds to the specific antibody attached to the polystyrene dish. Unbound sample is washed out with buffer. A reporter antibody specifically directed to hESF I and linked to horseradish peroxidase is placed in the dish resulting in binding of the reporter antibody to any monoclonal antibody bound to hESF I. Unattached reporter antibody is then washed out. Reagents for peroxidase activity, including a calorimetric substrate are then added to the dish. Immobilized peroxidase, linked to hESF I antibodies, produces a colored reaction product. The amount of color developed in a given time period is proportional to the amount of hESF I protein present in the sample. Quantitative results typically are obtained by reference to a standard curve. Without limiting the instant invention, typically, for a quantitative diagnostic assay a positive result or abnormally high level indicating the disease is one in which blood levels are higher than three standard deviations above the mean blood level for a normal healthy population of individuals (99.86% of the population).

A competition assay may be employed wherein antibodies specific to hESF I attached to a solid support and labeled hESF I and a sample derived from the host are passed over the solid support and the amount of label detected attached to the solid support can be correlated to a quantity of hESF in the sample.

Nucleic acid methods can also be used to detect transcription levels of hESF I as a marker for abnormal cell growth indicative of endometrial cancer and/or uterine cancer. Polymerase chain reaction (PCR) and other nucleic acid methods, such as ligase chain reaction (LCR) and nucleic acid sequence based amplification (NASABA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones arrayed on a grid can be used to both detect the expression of and quantitate the level of expression of that gene (gridding). In this approach, a cDNA encoding the hESF I gene is fixed to a substrate. The substrate may be of any suitable type including but not limited to glass, nitrocellulose, nylon or plastic. DNA encoding the hESF I clone is attached to the substrate and then incubated with the analyte, which may be RNA or a complementary DNA (cDNA) copy of the RNA, isolated from the tissue of interest. Hybridization between the substrate bound clone and the analyte can be detected and quantitated by several means including, but not limited to, radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

The above tests can be carried out on samples derived from patients' bodily fluids and tissue extracts (homogenates or solubilized tissue) such as from blood, urine, saliva, tissue biopsy and autopsy material. Levels of hESF I, determined in cells, tissues or a bodily fluid from a patient suspected of suffering from endometrial or uterine cancer by measuring the polypeptide or by transcription levels, are compared to levels of hESF I in normal or control cells, tissue or bodily fluids. Elevated levels of hESF I measured in the patient as compared to levels in the same cells, tissues or bodily fluids obtained from normal, healthy individuals are indicative of endometrial cancer and/or uterine cancer. By "elevated levels" it is meant at least approximately a 2-fold increase in measured hESF I levels in a patient as compared to hESF I levels in the same normal cells, tissues or bodily fluids. Detection of elevated hESF I levels is useful in the diagnosis of both endometrial and uterine cancer.

Further, monitoring of hESF I levels in a patient diagnosed with endometrial and/or uterine cancer is useful in determining the onset of metastases in cancers which have not yet metastasized and in determining the stage of the cancer. For example, detection of hESF I can be used in a method of monitoring endometrial cancer or uterine cancer in a patient which has not metastasized for the onset of metastasis. In this method, a patient suffering from endometrial cancer or uterine cancer that is not known to have metastasized is identified. hESF I levels in a sample of bodily fluid from the patient are then measured. These measured hESF I levels are then compared with levels of hESF I in the same bodily fluid type from a normal control sample. An increase in measured hESF I levels in the patient versus the normal control is associated with a cancer which has metastasized.

The stage of endometrial cancer or uterine cancer in a patient suffering from endometrial cancer or uterine cancer can also be determined. In this method a patient suffering from endometrial cancer or uterine cancer is identified. hESF I levels in a sample of bodily fluid from the patient are measured to establish a baseline hESF I level for said patient. hESF I levels in samples of the same bodily fluid are then determined at subsequent time periods such as scheduled check-ups with the patient's physician. Measured hESF I levels are then compared with the baseline hESF I levels for the patient. In this method, an increase in measured hESF I levels in the patient versus baseline hESF I levels in the patient is associated with a cancer which is progressing and a decrease in measured hESF I levels versus baseline hESF I levels is associated with a cancer which is regressing or in remission. Increases in measured hESF I levels as compared to baseline hESF I levels established for the patient may also be indicative of metastases.

EXAMPLES

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

All examples are carried out using standard techniques, which are well known and routine to those of skill in the art, except where otherwise described in detail. Routine molecular biology techniques of the following examples can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989), herein referred to as "Sambrook."

All parts or amounts set out in the following examples are by weight, unless otherwise specified.

Unless otherwise stated size separation of fragments in the examples below is carried out using standard techniques of agarose and polyacrylamide gel electrophoresis ("PAGE") in Sambrook and numerous other references such as, for instance, by Goeddel et al., *Nucleic Acids Res.* 8:4057 (1980).

Example 1 hESF I Tissue Distribution

To determine the tissue distribution of hESF I expression, mRNA and cDNA was prepared from a variety of tissues and the polymerase chain reaction was done using the hESF I primers. Results are indicated below:

| TISSUE | RESULT OF RT-PCR REACTION |
| --- | --- |
| Endometrial Normal A | Absent |
| Endometrial Normal B | + |
| Endometrial Normal C | Absent |
| Endometrial Cancer A | ++++ |
| Endometrial Cancer B | ++++ |
| Endometrial Cancer C | ++++ |
| Colon Normal A | Absent |
| Colon Cancer A | Absent |
| Colon Normal B | Absent |
| Colon Cancer B | Absent |
| Liver Normal | Absent |
| Liver Cancer | Absent |
| Mammary Gland | Absent |
| Pancreas | Absent |
| Prostate A | ++++ |
| Prostate B | ++++ |
| Liver | Absent |
| Uterus | ++++ |
| Heart | Absent |
| Skeletal Muscle | Absent |
| White blood Cells | Absent |
| Lung Normal A | Absent |
| Lung Cancer A | Absent |
| Lung Normal B | Absent |
| Lung Cancer B | Absent |

Example 2

Relative Quantitation of Gene Expression.

Real-Time quantitative PCR with fluorescent TaqMan probes is a quantitation detection system utilizing the 5'-3' nuclease activity of Taq DNA polymerase. The method uses an internal fluorescent oligonucleotide probe (TaqMan) labeled with a 5' reporter dye and a downstream, 3' quencher dye. During PCR, the 5'-3' nuclease activity of Taq DNA polymerase releases the reporter, whose fluorescence can then be detected by the laser detector of the Model 7700 Sequence Detection System (PE Applied Biosystems, Foster City, Calif., USA).

Amplification of an endogenous control is used to standardize the amount of sample RNA added to the reaction and normalize for Reverse Transcriptase (RT) efficiency. Either cyclophilin, glyceraldehyde-3-phosphate dehydrogenase (GAPDH) or 18S ribosomal RNA (rRNA) is used as this endogenous control. To calculate relative quantitation between all the samples studied, the target RNA levels for one sample is used as the basis for comparative results (calibrator). Quantitation relative to the "calibrator" can be obtained using the standard curve method or the comparative method (User Bulletin #2: ABI PRISM 7700 Sequence Detection System).

To evaluate the tissue distribution, and the level of hESF I in normal and tumor tissue, total RNA was extracted from normal tissues, tumor tissues, and from tumors and the corresponding matched normal tissues. Subsequently, first strand cDNA was prepared with reverse transcriptase and the polymerase chain reaction was done using primers and TaqMan probe specific to hESF I. The results are analyzed using the ABI PRISM 7700 Sequence Detector. The absolute numbers are relative levels of expression of HESF I compared to the calibrator.

The absolute numbers are relative levels of expression in 12 normal tissues of HESF I compared to thymus (calibrator). These RNA samples are originated by pooling samples from a particular tissue from different individuals.

| Tissue | NORMAL |
| --- | --- |
| Brain | 0.3 |
| Heart | 0.1 |
| Kidney | 0.1 |
| Liver | 0.3 |
| Breast | 0.1 |
| Prostate | 1.2 |
| Small | 0.1 |
| Spleen | 0.2 |
| Testis | 43.3 |
| Thymus | 1.0 |
| Uterus | 698.0 |

The relative levels of expression show that hESF I mRNA expression is more than 10 fold higher in the pool of normal uterus (698) compared with the other 12 normal tissues of pooled samples analyzed. Testis, the second higher expressor at 43.3 is a male tissue, and will not represent a problem for diagnosis of endometrial or uterine cancer. These results demonstrate that hESF I mRNA expression is highly specific for uterus, a tissue that is mainly composed of endometrium.

The absolute numbers correspond to pools of samples from different individuals. They can not be compared to the absolute numbers originated from samples of a single individual in the following table.

In the following table, the absolute numbers are relative levels of expression of hESF I compared to thymus (calibrator), in 36 pairs of matching samples. Each matching pair contains the cancer sample for a particular tissue and the normal adjacent sample for that same tissue from the same individual.

| Tissue | CANCER | MATCHING NORMAL |
| --- | --- | --- |
| Endometrium 1 | 0.0 | 1.0 |
| Endometrium 2 | 3641.1 | 505.5 |
| Endometrium 3 | 2.9 | 1120.6 |
| Endometrium 4 | 27.4 | 92.1 |
| Endometrium 5 | 156.0 | 346.1 |
| Endometrium 6 | 566.1 | 115.4 |
| Endometrium 7 | 405684.9 | 907.0 |
| Endometrium 8 | 3.7 | 7.5 |
| Endometrium 9 | 95.1 | 47.6 |
| Breast | 0.2 | 3.1 |
| Breast | 0.0 | 13.5 |
| Breast | Neg. | 2.3 |
| Breast | Neg. | Neg. |
| Ovary | 0.1 | 0.1 |
| Ovary | 0.7 | 14.5 |
| Prostate | 0.4 | 0.2 |
| Prostate | 0.1 | 0.2 |
| Prostate | 0.1 | 0.0 |
| Prostate | Neg. | Neg. |
| Bladder | Neg. | Neg. |
| Bladder | 0.8 | 11.2 |
| Colon | Neg. | Neg. |
| Colon | Neg. | Neg. |
| Kidney | Neg. | Neg. |
| Liver | 0.1 | 0.1 |
| Lung | Neg. | 0.1 |
| Lung | Neg. | Neg. |
| Lung | 0.3 | 1.4 |
| Pancreas | Neg. | Neg. |
| Pancreas | Neg. | Neg. |
| Small | Neg. | Neg. |
| Testis | 4.1 | 2.0 |
| Uterus 1 | 8.3 | 16.4 |
| Uterus 2 | 25.3 | 0.8 |
| Uterus 3 | 5.4 | 44.7 |
| Uterus 4 | 125.4 | 20.5 |

Neg. = Negative

When matching samples were analyzed, the higher levels of expression were in endometrium and uterus showing a high degree of tissue specificity for these two tissues. These results confirm the tissue specificity results obtained with normal samples. Furthermore, the level of mRNA expression in cancer samples and the isogenic normal adjacent tissue were compared from the same individual. These data show overexpression of hESF I in endometrial cancer tissues number 2, 6, 7 and 9 compared with the corresponding normal adjacent tissue. Similarly, overexpression in cancer is observed for the uterine samples number 2 and 4. Previous mRNA expression analysis for genes coding for the diagnostic markers PSA and PLA2 showed overexpression of the mRNA in 40% to 80% of the matching samples analyzed.

Altogether, the high level of tissue specificity, plus the mRNA overexpression in almost half of the endometrial and uterine matching samples tested demonstrate that hESF I is a good diagnostic marker for endometrial and uterine cancer.

What is claimed is:

1. A method for detecting the expression of the cancer marker hESF I in a patient comprising:
   (a) taking a sample derived from a patient; and
   (b) detecting in the sample a nucleic acid sequence encoding hESF I or a protein product encoded by a hESF I nucleic acid sequence.

2. A diagnostic method for detecting the presence of endometrial cancer or uterine cancer in a patient suspected of suffering from endometrial cancer or uterine cancer comprising:
   (a) measuring levels of hESF I polypeptide in cells, tissues or bodily fluids obtained from a patient suspected of suffering from endometrial cancer or uterine cancer; and (b) comparing the measured levels with levels of hESF I in normal cells, tissues or bodily fluids, wherein an increase in hESF I levels in the patient versus levels of hESF I in normal cells, tissues or bodily fluids is indicative of endometrial cancer or uterine cancer.

3. A diagnostic method for detecting the presence of endometrial cancer or uterine cancer in a patient suspected of suffering from endometrial cancer or uterine cancer comprising:

(a) measuring transcription levels of hESF I in cells, tissues or bodily fluids of a patient suspected of suffering from endometrial or uterine cancer; and (b) comparing the measured transcription levels of hESF I with hESF I transcription levels in normal cells, tissues or bodily fluids, wherein an increase in hESF I transcription levels in the patient versus normal hESF I transcription levels is associated with endometrial cancer or uterine cancer.

4. A method of monitoring endometrial cancer or uterine cancer in a patient which has not metastasized for the onset of metastasis comprising:

(a) identifying a patient suffering from endometrial cancer or uterine cancer that is not known to have metastasized;

(b) measuring hESF I levels in a sample of bodily fluid from said patient; and (c) comparing the measured hESF I levels in said patient with levels of hESF I in the same bodily fluid type from a normal control sample, wherein an increase in measured hESF I levels in the patient versus the normal control is associated with a cancer which has metastasized.

5. A method of monitoring the stage of endometrial cancer or uterine cancer in a patient suffering from endometrial cancer or uterine cancer comprising:

(a) identifying a patient suffering from endometrial cancer or uterine cancer;

(b) determining hESF I levels in a sample of bodily fluid from said patient to establish a baseline hESF I level for said patient;

(c) measuring hESF I levels in samples of the same bodily fluid from said patient at subsequent time periods; and (d) comparing the measured hESF I levels with the baseline hESF I levels, wherein an increase in measured hESF I levels in the patient versus baseline hESF I levels in the patient is associated with a cancer which is progressing and a decrease in measured hESF I levels versus baseline hESF I levels is associated with a cancer which is regressing or in remission.

6. The method of claim 5 wherein an increase in measured hESF I levels in the patient versus baseline hESF I levels in the patient is associated with the cancer having metastasized.

* * * * *

UNITED STATES PATENT AND TRADEMARK OFFICE
CERTIFICATE OF CORRECTION

PATENT NO.     : 6,228,596 B1                                           Page 1 of 1
DATED          : May 9, 2001
INVENTOR(S)    : Macina and Burczak It is certified that error appears in the above-identified patent and that said Letters Patent is hereby corrected as shown below:

Column 7,
In the Table, between lines 35 to 47, between the entries of "Liver 0.3" and "Breast 0.1", please insert -- Lung          0.1 --.

Signed and Sealed this

Sixth Day of May, 2003

JAMES E. ROGAN
*Director of the United States Patent and Trademark Office*